US012251517B2

(12) United States Patent
Huss

(10) Patent No.: US 12,251,517 B2
(45) Date of Patent: Mar. 18, 2025

(54) EAR MOUNTED CANNULAR NASAL BREATHING FILTER

(71) Applicant: Leland H. Huss, Concord, CA (US)

(72) Inventor: Leland H. Huss, Concord, CA (US)

( * ) Notice: Subject to any disclaimer, the term of this patent is extended or adjusted under 35 U.S.C. 154(b) by 784 days.

(21) Appl. No.: 17/519,231

(22) Filed: Nov. 4, 2021

(65) Prior Publication Data

US 2022/0054786 A1    Feb. 24, 2022

Related U.S. Application Data

(60) Provisional application No. 63/110,870, filed on Nov. 6, 2020.

(51) Int. Cl.
*A61M 16/06*    (2006.01)
*A61M 16/00*    (2006.01)
(Continued)

(52) U.S. Cl.
CPC .... *A61M 16/0683* (2013.01); *A61M 16/0666* (2013.01); *A61M 16/1045* (2013.01);
(Continued)

(58) Field of Classification Search
CPC .......... A61M 16/0666; A61M 16/0683; A61M 16/105; A61M 16/107; A61M 16/0688;
(Continued)

(56) References Cited

U.S. PATENT DOCUMENTS 5,647,345 A * 7/1997 Saul .................. A61M 16/0045
128/200.24

6,377,697 B1 * 4/2002 Cheng .................... H04R 1/083
381/381
(Continued)

FOREIGN PATENT DOCUMENTS

| CN | 111803818 A | * | 10/2020 | ............. A62B 23/06 |
| KR | 101461173 B1 | * | 12/2014 | ............... A62B 7/10 |
| KR | 101739568 B1 | * | 5/2017 | ............. A62B 23/06 |

OTHER PUBLICATIONS

KR101461173B1 machine translation accessed Oct. 3, 2024 (Year: 2024).*

(Continued)

*Primary Examiner* — Bradley H Philips
*Assistant Examiner* — Kelsey Rhee
(74) *Attorney, Agent, or Firm* — Steven A. Nielsen; www.NielsenPatents.com

(57) ABSTRACT

An ear mounted cannular nasal breathing filter provides an air mixing chamber to offset the effects of dry air caused by filtration by allowing for an admixture of filtered and pre-conditioned (humidified and heated) air. The air chamber features an internal or centered mixing chamber disposed below a one-way exhaust valve and above a filtering system. The air mixing chamber retains a predefined volume or percentage of exhausted breath that is mixed with a predefined volume or percentage of filtered air, with the filtered air originating as ambient air. An air chamber assembly is retained and supported upon a user by an ear mount system comprising a) a flexible wire that conforms to the ear join, or b) an upper arm in telescopic connection with a lower arm, with the two arms in dynamic tension by use of an internal elastic member, providing a tensioned fit to the ear join.

6 Claims, 18 Drawing Sheets

(51) Int. Cl.
- *A61M 16/10* (2006.01)
- *A61M 16/20* (2006.01)
- *A62B 23/06* (2006.01)

(52) U.S. Cl.
CPC ........ *A61M 16/105* (2013.01); *A61M 16/208* (2013.01); *A62B 23/06* (2013.01); *A61M 16/0045* (2013.01); *A61M 2205/7545* (2013.01); *A61M 2210/0662* (2013.01)

(58) Field of Classification Search
CPC ...... A61M 16/0694; A61M 2210/0662; A61M 16/0672–0677; A61M 15/085; A61M 15/08; A61M 16/0045; A61M 16/1045; A62B 23/06; A62B 18/084; A41D 13/1161; H04R 1/105; A61B 5/6815; A61F 11/06; A61F 11/14
See application file for complete search history.

(56) References Cited

U.S. PATENT DOCUMENTS

| | | | | |
|---|---|---|---|---|
| 11,771,930 | B1* | 10/2023 | Shah | A62B 23/06 128/206.11 |
| 2015/0068530 | A1* | 3/2015 | Apolito | A61M 16/0683 128/207.18 |
| 2015/0174435 | A1* | 6/2015 | Jones | A62B 18/10 128/202.13 |

OTHER PUBLICATIONS

KR101739568B1 machine translation accessed Oct. 3, 2024 (Year: 2024).*

CN111803818A machine translation accessed Feb. 6, 2025 (Year: 2025).*

* cited by examiner

EAR MOUNTED CANNULAR NASAL BREATHING FILTER

CROSS-REFERENCE TO RELATED APPLICATIONS

This utility patent applications claims the benefit and priority date of provisional patent application 63/110,870 filed on Nov. 6, 2020, the contents of which are incorporated herein by reference.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

BACKGROUND OF THE INVENTION

(1) Field of the Invention

The invention generally relates to personal air filtration systems. More particularly, the invention relates to means and methods of creating an ear mounted air filter with a cannular nasal input and with a system of mixing filtered ambient air with precondition air.

(2) Description of the Related Art

Large populations around the globe suffer from harmful particulates inhaled from the air they breathe. Such airborne particulates arise from industrial pollution, vehicle emissions, the burning of refuse, events such as wildfires, and other sources. Medical science learns more each passing year on how harmful the particulate matter from these sources are to human health, yet there are few solutions available to individuals to mitigate this health risk. Other than high-grade, properly fitting, rated masks (which lack the comfort and convenience people need in their daily lives), there are only a few nasal based filters in the known prior art which are unfortunately of very limited effectiveness and quality. There are no real options in the known prior art that provide the protective effectiveness of masks, but with the convenience of a nasal filter, which allows for activities such as speaking clearly, eating, and drinking while breathing protection remains in place.

For a breathing filter to be effective, it requires four primary design features:
1. Effective sealing—so that outside air is drawn through the filtering mechanism itself and allows in very little, if no, unfiltered air into each breath.
2. Sufficient air flow—through the device so that enough air can be processed by the filter without needing to strain for breaths or only getting partial breaths.
3. Sufficient filter surface area—to both provide for sufficient air flow while also allowing for a filter of rated and standard effectiveness to be used (i.e. a filter of recognized effectiveness, such as a PM 2.5 filter).
4. Rated filter materials—that are recognized to provide effective filtering of airborne particulates and feature sufficient filter lifespans.

There are currently no known prior art nasal breathing filters that fulfill these four requirements. The Ear Mounted Cannular Nasal Breathing Filter (sometimes referred to as "the presently disclosed embodiments" or "the invention") presented herein provides for all four requirements above via nasal breathing, and also provides the comfort and convenience people need in their daily lives to encourage consistent use. Additionally, the lightweight and ergonomic designs of the disclosed embodiments provide for a wide range of useability while minimizing "use fatigue", thus encouraging general everyday use and use during physical activity.

In the known related art, breathing filters for individuals primarily consist of three modalities:
1. Properly fitting/sealing filtering facial masks, such as N-rated masks (N95, N99, etc.), that provide effective protection and a good filter lifespan.
2. Loosely fitting cloth facial coverings with PM-rated filter inserts that provide very limited filtering effectiveness due to the lack of a proper seal and a porous cloth design.
3. Intra-nasal filter units that fit inside the nostrils and generally provide a good seal but have 'filters' that are either totally ineffective gimmicks or are only mildly effective at best and provide very limited protection from harmful airborne particulates. Such Ineffective filtering is due, in part, to the very small surface area of such filters and that these filters do not feature any standard or rated filter materials. Such filters usually comprise a cotton film, permeable foam, or a very thin electrostatic membrane; all of which provide either no or very limited filtering capability with a very limited filter lifespan. Additionally, many of these types of filters are single use, creating additional costs to users and unnecessary environmental waste.

The benefits of properly fitting, rated filtering masks are critical in protection and lifespan, but they unfortunately lack the convenience and comfort people need in their daily lives. Loosely fitting cloth masks with filter inserts provide comfort, but greatly lack protective effectiveness and still lack convenience (filter lifespan is irrelevant due to the lack of a proper seal). Intra-nasal filters of the known prior art provide both comfort and convenience, but either completely lack protective effectiveness or provide very little protection with a very limited lifespan.

BRIEF SUMMARY OF THE DISCLOSED EMBODIMENTS

Disclosed embodiments may comprise an air chamber of sufficient size and configuration such that exhaled breaths are partially recycled to provide an admixture with newly inhaled air to compose a mix of pre-conditioned and fresh, filtered air. The device may comprise a plurality of air volume capacities, but as an example we'll consider a device that has 50 cubic centimeters (cc's) of air volume capacity, as sometimes defined by the internal volume of the air chamber, breathing tube, and nasal cannula.

The average 'tidal volume' (i.e. amount of air inhaled and exhaled out of the lungs with each respiratory cycle when breathing normally) is around 500 mL for a healthy adult male and around 400 mL for a healthy adult female. For this example we'll go with the upper limit of the average and assume a tidal volume of 500 mL.

Disclosed embodiments may have an air volume capacity of 50 cc's, and as one cc is equal to 1 mL, upon exhalation the user would push all the air in the system out through the One-way Valve, leaving 50 mL of exhaled, and thereby pre-conditioned (i.e. humidified and heated), air in the system.

Upon the subsequent inhalation, the user would draw in 450 mL of fresh air that would mix with the 50 mL of pre-conditioned air in the system, leading to an inhalation that contains 10% pre-conditioned air by volume. This admixture of fresh and pre-conditioned air will further help the lungs to utilize the air in each breath.

Additionally, since the fresh air is being drawn through a rated filter, the filter will dehumidify the ambient air, leading to dryer air being pulled into the system (as some of the moisture is captured by the filter). Since a portion of the exhaled air is being recycled and humidity is kept in the system, this keeps the filtered air from becoming dried out, which confers a benefit to the user as dry air is more difficult for the lungs to utilize.

By volume, inhaled air is about 20% oxygen while exhaled air is about 15% oxygen, meaning only a quarter of the available oxygen is absorbed in each breath. Given this, and that each breath introduces a majority by volume of fresh air, there is no risk of carbon dioxide build up during the respiratory cycle while using the disclosed embodiments.

The disclosed embodiments address the shortcomings of the above prior art modalities for filtration of airborne particulate matter while nasal breathing while providing additional benefits.

Disclosed embodiments may include an ergonomic ear mount, that may mount a disclosed device.

Thus, there is a need in the art for the presently disclosed embodiments on the head while providing for optimal placement, stability, and comfort.

The ear mount can be made of a firm but flexible 'wire' (i.e. rubber wire, solid core wire, etc.) that can easily be conformed to an individual's unique ear shape for maximum comfort, stability, and fit.

The ear mount can also be made of a solid frame (such as plastic) featuring a tensioning system that provides mild pressure from the bottom of the ear mount (i.e. tensioning the lower arm of the ear mount), both increasing stability and providing for a customized fit for the user.

The disclosed embodiments include a specialized and special purpose air chamber which may comprise a chamber attached to the ear mount that features a filter mount on one end and a one-way air valve on the other end, and rests comfortably behind the ear. The air chamber also functions as an air reservoir to partially recycle the conditioned air (i.e. humidified and heated) of exhalation breaths. The air chamber is large enough to permit enough air flow to cycle with each breath to reduce moisture build up in the system during use. The air chamber features a curved tube extending out that serves as both a connector for the breathing tube and as a support for connecting with the ear mount.

The disclosed air chamber assembly may comprise or define a center chamber wherein exhausted air and filtered ambient air are mixed. The center chamber may be defined by the inner wall of the chamber assembly cylinder (or other volumetric shape), the bottom portion of the one-way valve and the upper portion of the air filter.

Disclosed embodiments may include a new and specialized filter mount which may comprise a rigid mount on the bottom of the air chamber that features ventilation gaps to provide for excellent filter air flow and a frame to mount and seal the air filter upon.

Disclosed embodiments may include a replaceable air filter, that may include a 'bag' filter (single closed-end sleeve-type filter, or simply a circular shape filter) made from standard, rated filter materials (such as PM 2.5), that slips over the filter mount and is sealed at the bottom of the mount, providing an air-tight seal.

This filter can be sealed by a number of systems or implements, such as several 'band' type fasteners such as a locking ring, cable tie, or a simple elastic band—all off of which provide for very easy filter replacement.

Disclosed embodiments may include a one-way valve that may be disposed within or upon the air chamber. The one-way valve provides effective air outflow on exhalation, so the user doesn't have to strain to push air out through the filter upon exhaling.

The valve can have a 'collar' around it to protect it from getting hair, etc. caught under the valve membrane thereby preventing an airtight seal.

Disclosed embodiments may include a breathing tube that may connect to an air chamber and provide air flow to the cannular nasal insert, with the breathing tube bridging across the cheek of a user. The breathing tube may comprise an 'accordion' section that allows the tube to extend or retract in length to provide a customized fit for the user, or any other method of length modification.

Disclosed embodiments may include a nasal cannula that may connect to a breathing tube and comprise or feature an 'inverted cup' type flange on each of the nasal insert prongs, which provides for an intra-nasal airtight seal while also providing mounting support to keep the cannula secured in place below the nose.

These flanges can come in multiple shapes (i.e. round, oval, etc.) to accommodate different shaped and sized nostrils.

Disclosed embodiments may include one or more cannula plugs, with such plugs being airtight or near airtight and may be disposed upon the cannula opposite to the breathing tube connection, which can be removed and allows for removal of excess moisture after prolonged use and to dehumidify when not in use.

Disclosed embodiments may include a tensioned ear mount that:

May comprise a solid body ear mount (as opposed to a flexible mount) that features a spring or elastic band connected to a lower arm that provides an automatically adjusting and tensioned fit.

Upper arm: The upper arm of the assembly fits over the top of the ear at the ear join and features a fitted hollow inset to accept a tang featured on the lower arm of the assembly. The inset may contain a tension anchor mount, to which the tensioning element attaches.

Lower arm: The lower arm of the assembly fits underneath the ear and provides upward tension to the lower ear join, providing an auto-adjusting, snug fit. Features a tang that enters the upper arm hollow inset and attaches to the tensioning system via a tension anchor mount. The lower arm features ergonomic shaping to provide for better fit and comfort.

Tensioning system: The tensioning system joins the upper arm and lower arm by means of a spring or elastic band, hooking into tension anchor mounts on each end. This allows the lower arm to move up and down as needed to provide a tensioned fit to the lower ear join, guided by the fitting of the lower arm tang into the upper arm hollow inset.

The disclosed embodiments overcome shortfalls in the related art by using the disclosed ergonomic ear mount, air chamber, filter mount, replaceable air filter, one-way valve, breathing tube, nasal cannula plug and other components and methods as further described herein.

The disclosed embodiments also overcome shortfalls in the known related art by mixing optimal ratios of breath exhaust with fresh filtered air. Thus, a user enjoys prehumified and warmed air optimally mixed as disclosed herein.

The disclosed embodiments also overcome shortfalls in the known related art by providing an ergonomic ear mount featuring a self-contained pre-tensioned system that may include a spring or other resilient member contained within a cavity, the cavity defined by an upper arm and lower arm, with the two arms in telescopic and dynamic connection with each other.

The disclosed embodiments overcome shortfalls in the related art by the configuration of the horizontal air intake pipe 270 in fluid connection with the vertical intake pipe 275 to so as to facilitate efficient mounting of the ear mount, so as to optimally position the air chamber assembly near the user's head.

These and other objects and advantages will be made apparent when considering the following detailed specification when taken in conjunction with the drawings.

Figure 1:
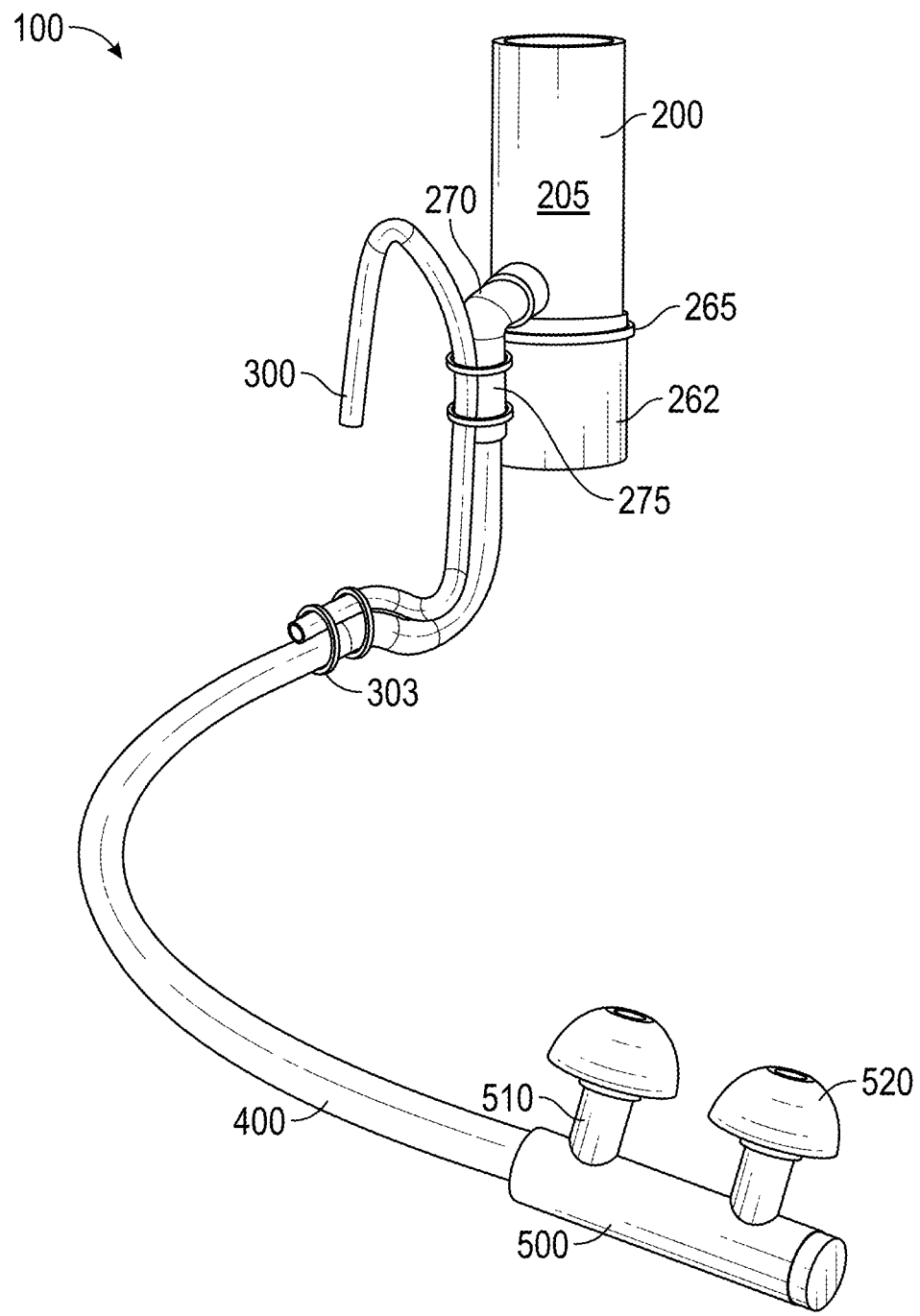
FIG. 1 depicts a perspective view of a disclosed embodiment

REFERENCE NUMERALS IN THE DRAWINGS 100 disclosed embodiment in general
200 air chamber assembly or air chamber housing
205 mixing chamber or center chamber of air chamber assembly
210 bottom void of air chamber
220 ventilation ports or ventilation voids defined by the air chamber assembly
225 breathing tube connector
240 filter mount
250 one-way valve
252 support structure for one way valve
255 support lip for air filter
260 air filter
262 preformed air filter
265 filter band fastener
270 horizontal air intake pipe
275 vertical air intake pipe
300 ear mount—flexible wire
303 ear mount attachment band
310 ear mount—solid body
320 upper arm of ear mount
325 loop or fastener within upper arm to secure spring 350
340 lower arm of ear mount
345 loop or fastener within lower arm to secure spring 350
350 spring, resilient member or tensioning system of ear mount 310
400 breathing tube or air tube
430 accordion segment of breathing tube
433 accordion segment in compression
435 accordion segment in expansion
500 nasal canula or nasal canula assembly
505 main body of nasal canula
510 prong posts
520 prong flanges
540 nasal plug or canula plug
"ear join" where the ear is connected to the user's head. An ear join or ear to head connection area may span from the upper section of an ear, back middle section and lower ear section.

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

Referring to FIG. 1, a disclosed system 100 may comprise an air chamber assembly 200 or air chamber housing 200 with the chamber housing comprising an outer shell, a preformed air filter 262 secured by a filter band fastener 265. A center chamber 205 of the chamber housing is in fluid connection with a horizontal air intake pipe 270, with the horizontal air intake pipe in fluid connection with a vertical air intake pipe.

The feature of the horizontal air intake pipe 270 being in fluid connection with the center or air mixing chamber 205 provides advantages over the known prior art by facilitating the mixture of exhaled air with fresh filtered air from the lower filter section. Exhaled air travels through the nasal canula assembly 500, through the breathing tube 400, through the vertical intake pipe 275, thought the horizontal intake pipe 270, and into the mixing chamber 205 with part of the exhaled air exiting though the upper one-way valve. Some of the exhaled air remains within the center chamber and prior fluid assembly components. Upon inhaling, the remaining exhaled air mixes with ambient air as the ambient air travels through the filter 262 and enters the mixing chamber 205. The act of inhaling creates a negative pressure within the air chamber assembly, drawing the one-way valve to a closed position as the one-way valve rests upon a frame structure just below the one-way valve.

The positioning of the horizontal intake pipe between the filter and one-way valve overcomes shortfalls in the related art by placing both exhaled air and freshly filtered ambient air into the center chamber 205, thus providing a user with a mixture to avoid the shortfall of breathing dried out, ambient temperature filtered air only.

Figure 2:
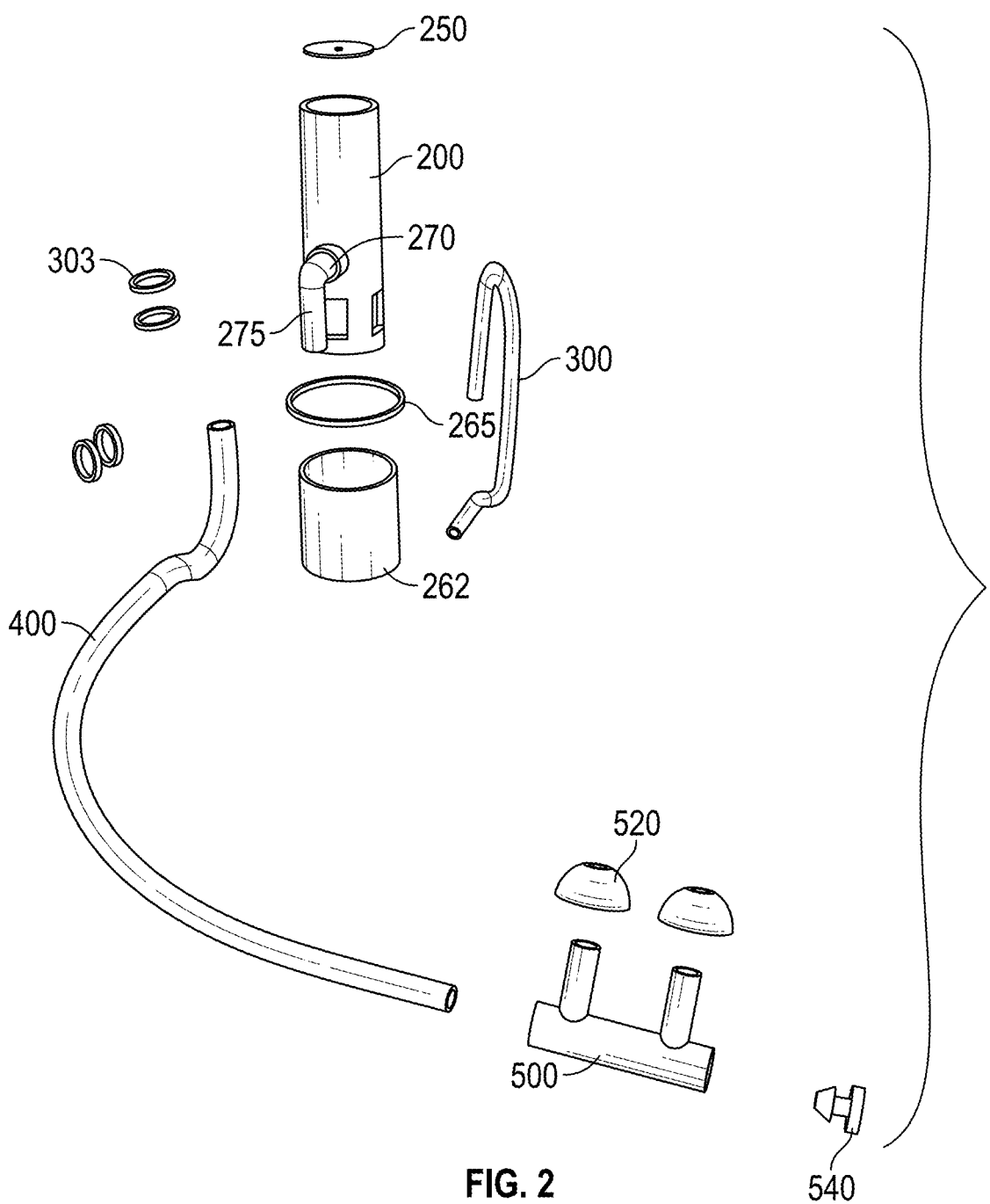
FIG. 2 depicts an exploded view of a disclosed embodiment

FIG. 2 is an expanded or blown-up rendition of FIG. 1.

Figure 3:
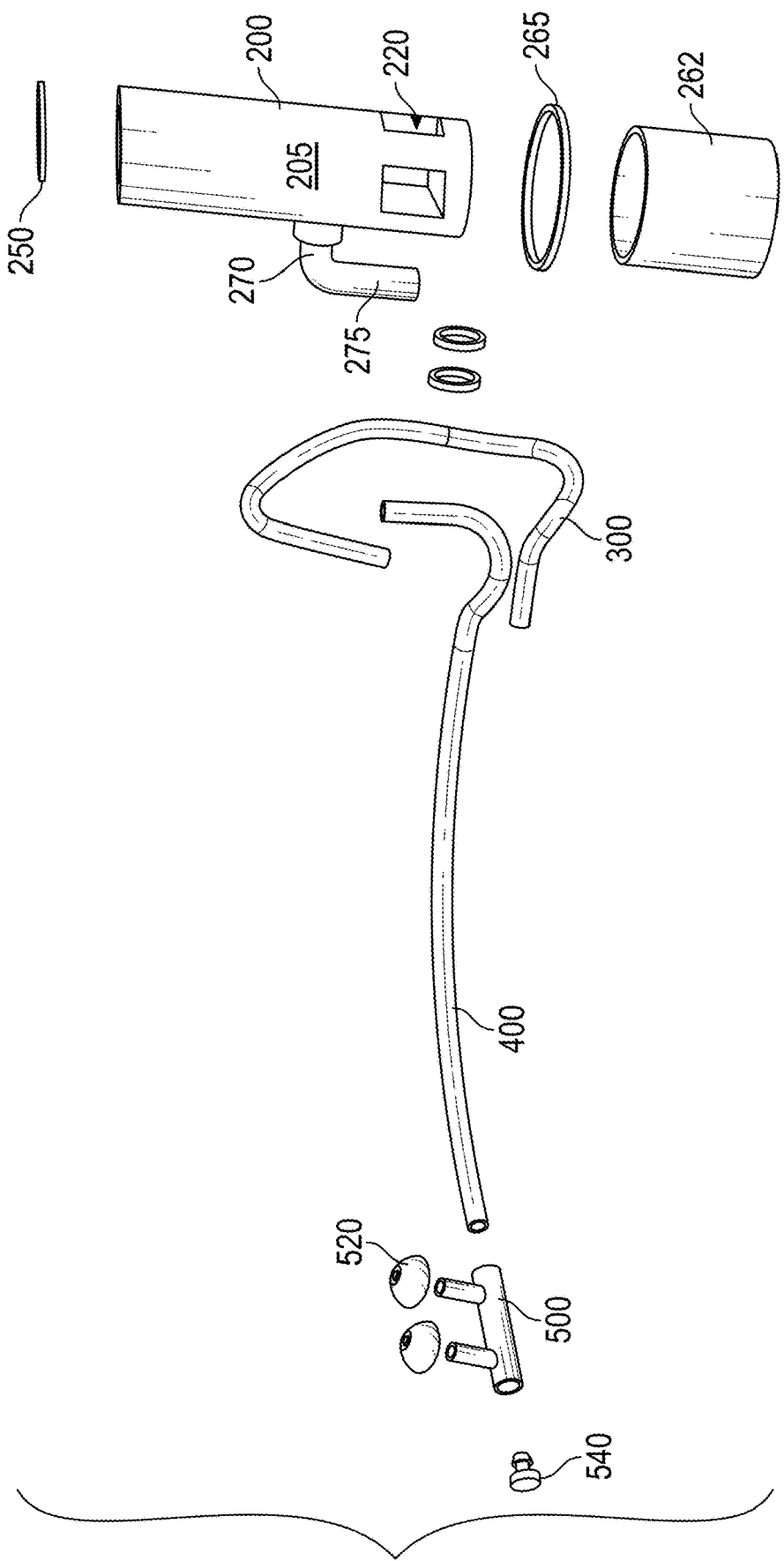
FIG. 3 depicts an exploded view of a disclosed embodiment

FIG. 3 is an exploded view of a disclosed embodiment and features clear views of the components comprising the air chamber assembly 200. The horizontal intake air pipe 270 is in fluid connection with the center or mixing void or mixing chamber 205 of the air chamber assembly.

Figure 4D:
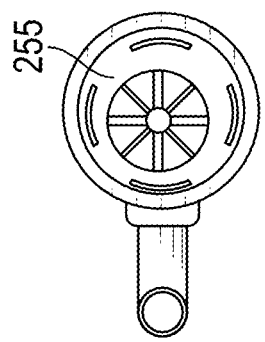
FIG. 4A perspective view of an air chamber housing
FIG. 4B perspective view of an air chamber housing
FIG. 4C top plan view of an air chamber housing
FIG. 4D bottom plan view of an air chamber housing
FIG. 5A elevation view of an ear mount
FIG. 5B sectional view of an ear mount
FIG. 6 exploded view of an ear mount
FIG. 7 perspective view of a disclosed embodiment
FIG. 8 sectional view of an ear mount
FIG. 9 sectional view of an air chamber assembly
Figure 4C:
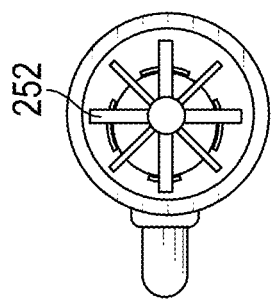
Figure 4B:
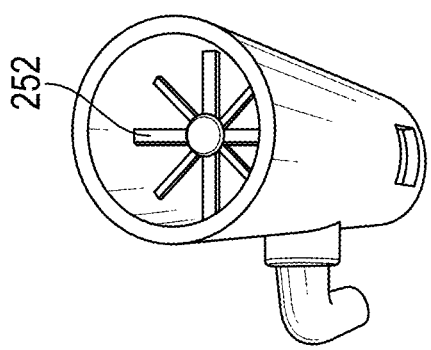
Figure 4A:
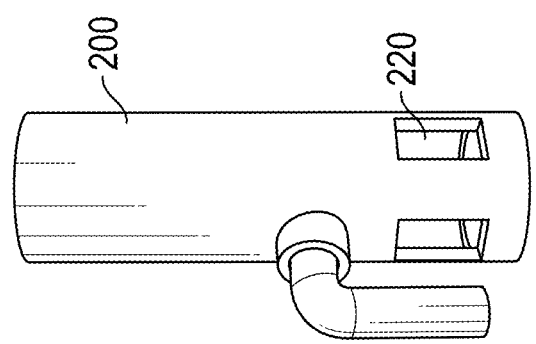

FIGS. 4A to 4D show various views of an air chamber assembly. FIG. 4D depicts a support lip 255 that may be used with a preformed filter.

Figure 5B:
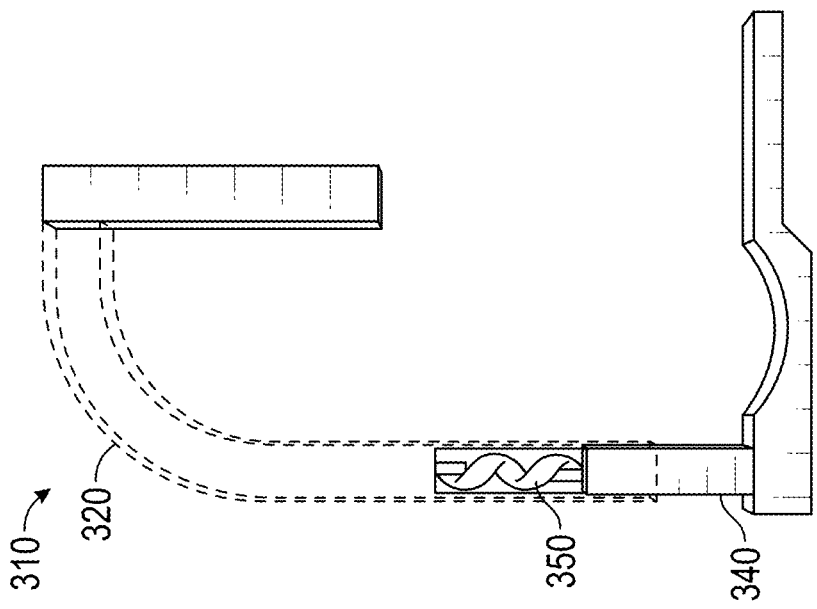
Figure 5A:
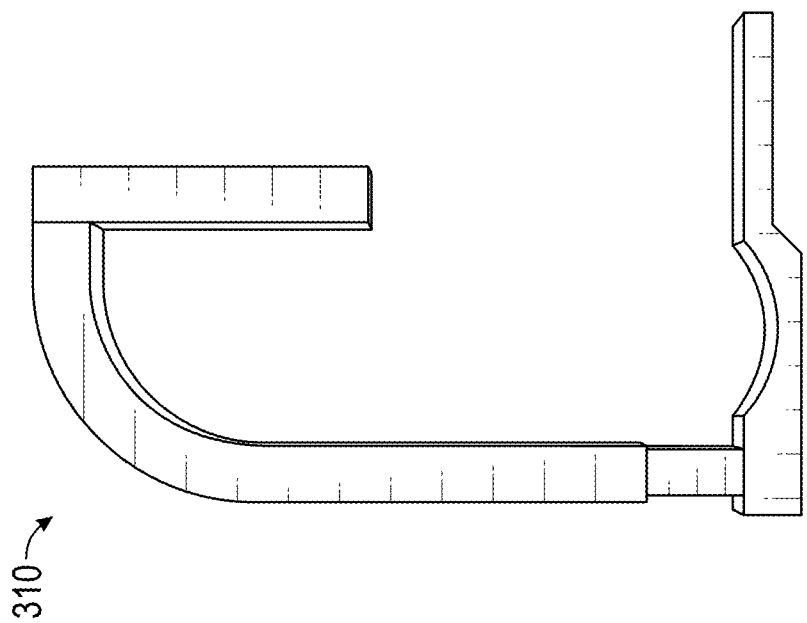

FIGS. 5A and 5B show a tensioning system of a solid ear mount 310 An internal resilient member 350 maintains elastic tension and elastic connection between an upper arm 320 and a lower arm 340.

Figure 6:
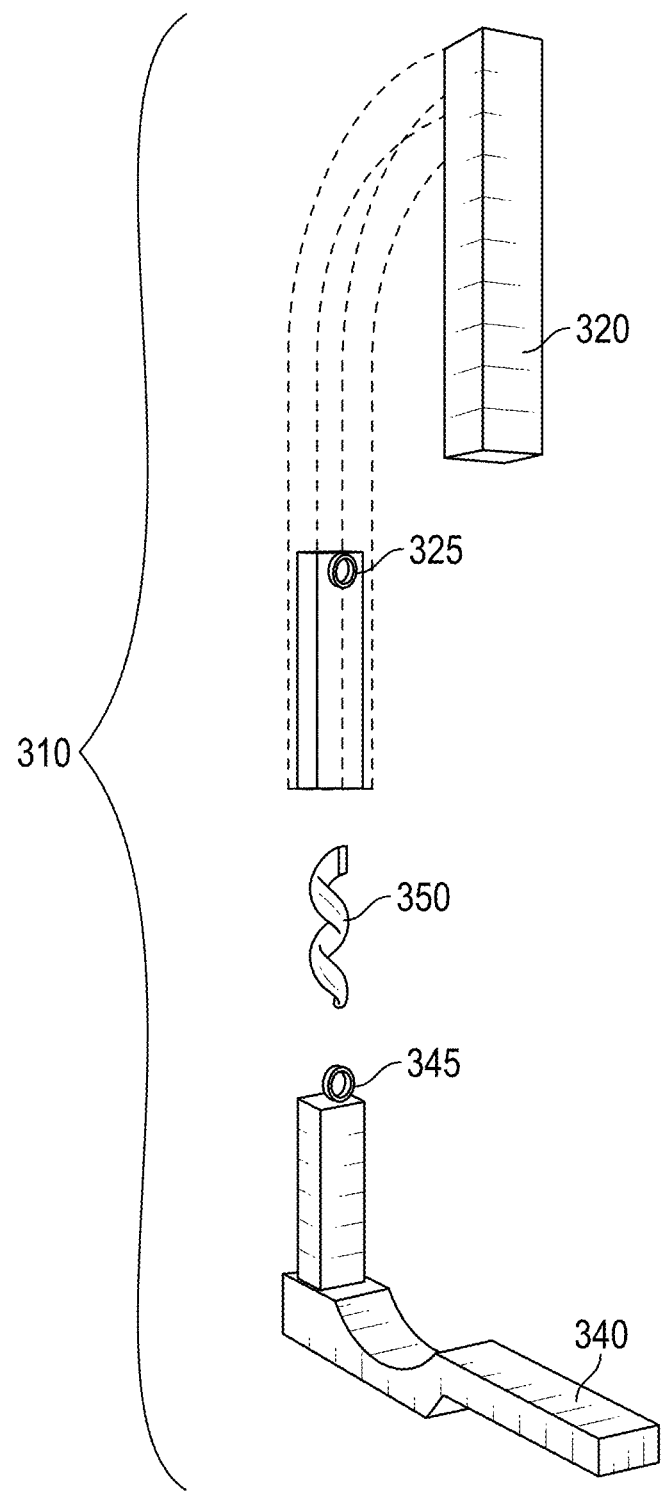

FIG. 6 shows an upper loop 325 and a lower loop 345 sometimes used to retain an internal resilient member 350.

The spring or resilient member 350 applies closing tension with the upper arm 320 and lower arm 340 such that the ear mount 310 as a whole rests upon and is fitted to the ear join or area where the ear is connected to the user's head. An ear join or ear to head connection area may span from the upper section of an ear, back middle section and lower ear section.

Figure 7:
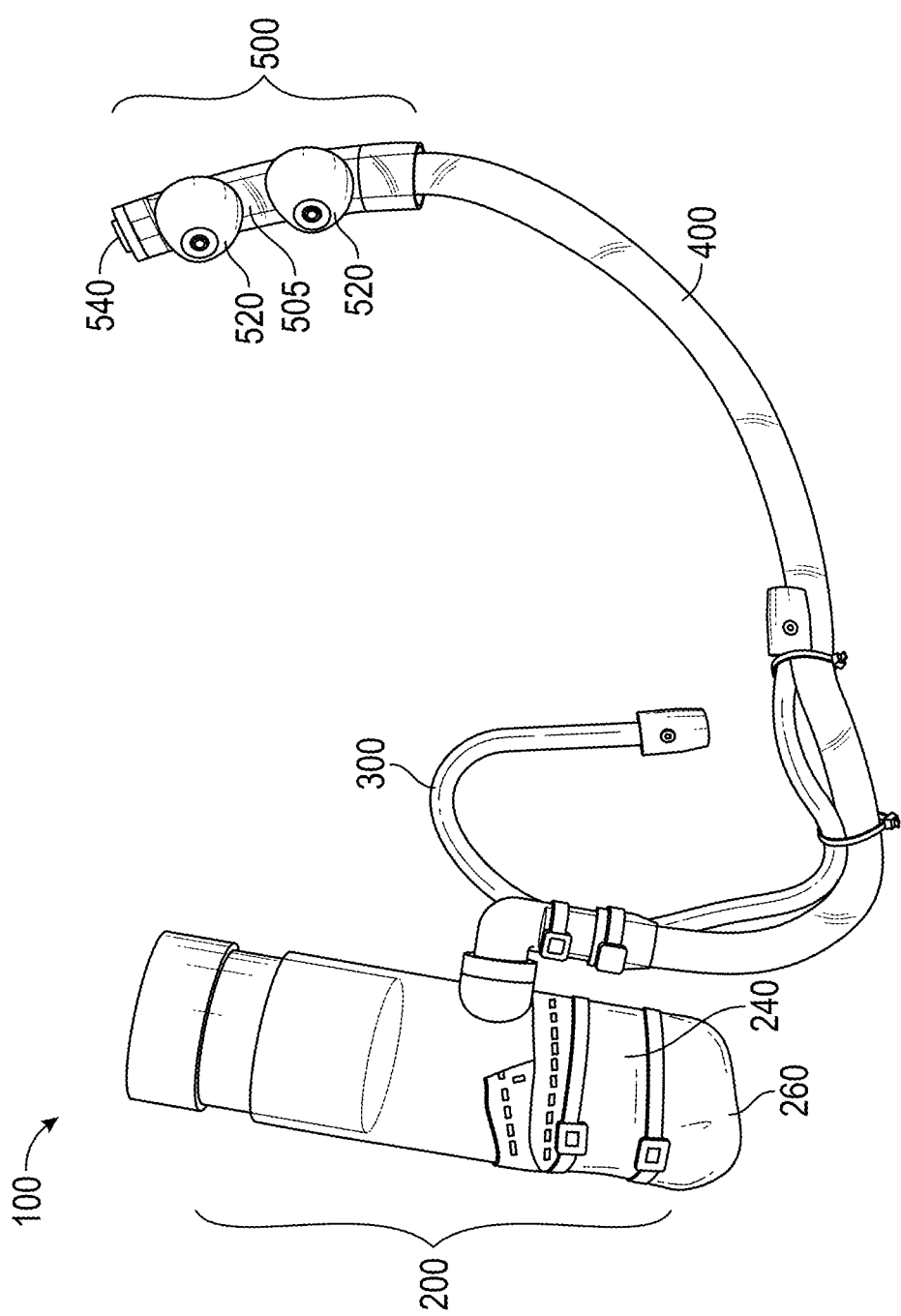

FIG. 7 depicts a disclosed embodiment 100 in general which may include an air chamber assembly 200, filter mount 240, cloth air filter 260, ear mount 300, breathing tube 400, nasal canula 500, prong flanges 520 and nasal plug 540.

Design features may include or comprise:

Ergonomic ear mount: Mounts the device on the head while providing for optimal placement, stability, and comfort.

An ear mount 300, referring to FIG. 7, can be made of a firm but flexible 'wire' (i.e. rubber wire, solid core wire, etc.) that can easily be conformed to an individual's unique ear shape for maximum comfort, stability, and fit.

Figure 8:
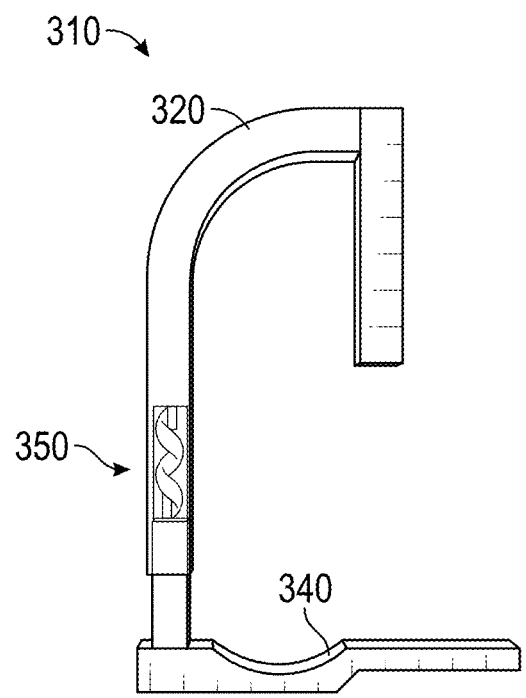

Referring to FIG. 8, a solid ear mount 310 may also be made of a solid frame (such as plastic) featuring a tensioning component 350 that provides mild pressure from the bottom of the ear mount (i.e. tensioning the lower arm 340 of the ear mount), both increasing stability and providing for a customized fit for the user. Additionally, other methods/configurations can be used to provide tensioning and fit. Upper arm of ear mount 320, may have a fitted hollow inset to accept a lower assembly tang, with upper tensioning system 350 resilient member. The ear mount may slip over top of ear and rests on top of an upper ear.

Still referring to FIG. 8, The lower arm 340 of ear mount, with tang that enters upper assembly hollow and attaches to tensioning system. Fits upward against bottom of ear.

A tensioning system 350 that joins upper and lower assemblies by means of an elastic band or spring tensioning system. This allows the lower assembly to move up and down as needed to provide a tensioned fit to the lower ear mount 340.

Figure 9:
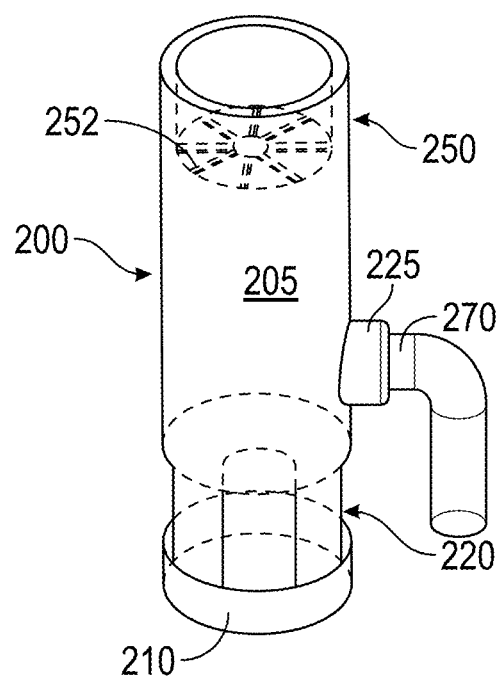

Referring to FIG. 9, an air chamber assembly 200 may be attached to an ear mount, an air chamber assembly may further comprise a filter mount on one end and a one-way air valve on the other end, and rests comfortably behind the ear. The air chamber also functions as an air reservoir to partially recycle the conditioned air (i.e. humidified and heated) of exhalation breaths. The air chamber is large enough to permit enough air flow to cycle with each breath to reduce excessive moisture build up in the system during use.

Referring to FIG. 9, a disclosed air chamber assembly 200 made as a single unit or housing (vs. two parts as in the prototype). An air chamber or air chamber assembly 200 may comprise an opening on bottom of air chamber 210 to allow for air flow. Ventilation ports 220 spaced around bottom of air chamber, i.e. the filter mount, to allow for additional air flow. In the top portion of the air chamber assembly a support structure 252 may span the internal void and provide support for a one-way valve. An optional breathing tube connector 225 may be in fluid connection with the mixing chamber 205 and a horizontal intake pipe 270.

Figure 10:
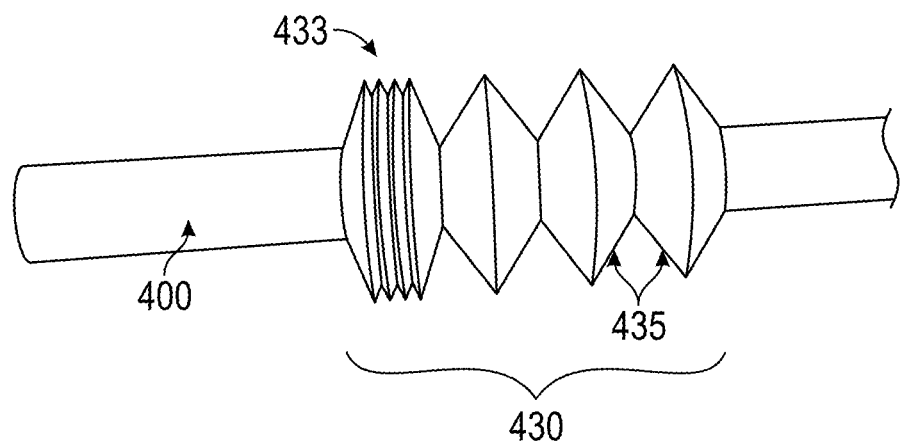
FIG. 10 depicts a perspective view of a breathing tube accordion segment

Referring to FIG. 10, the breathing tube can feature an 'accordion' section 430 that allows the tube to extend or retract in length to provide a customized fit for the user, or any other method of length modification. The accordion section may have parts in compression 433 or in expansion 435.

Figure 11:
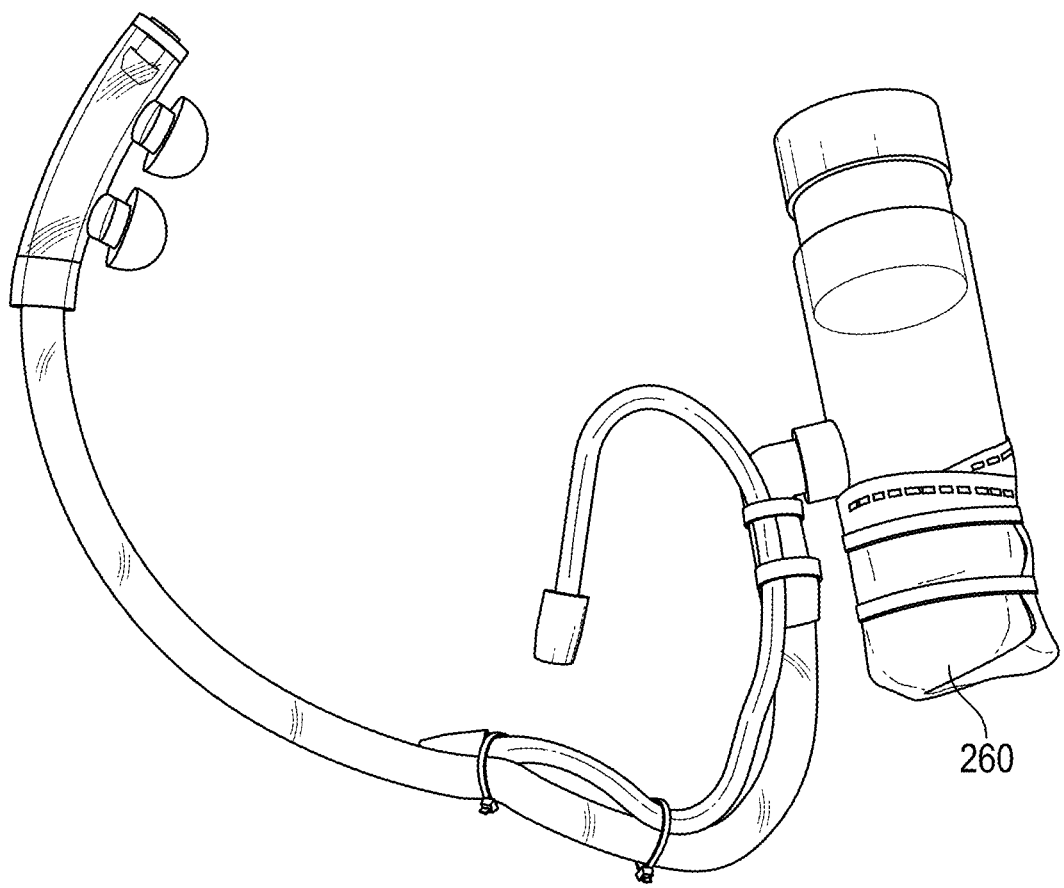
FIG. 11 depicts a perspective view of a disclosed embodiment

Referring to FIG. 11 a cloth filter 260 is used with an earlier embodiment.

Figure 12:
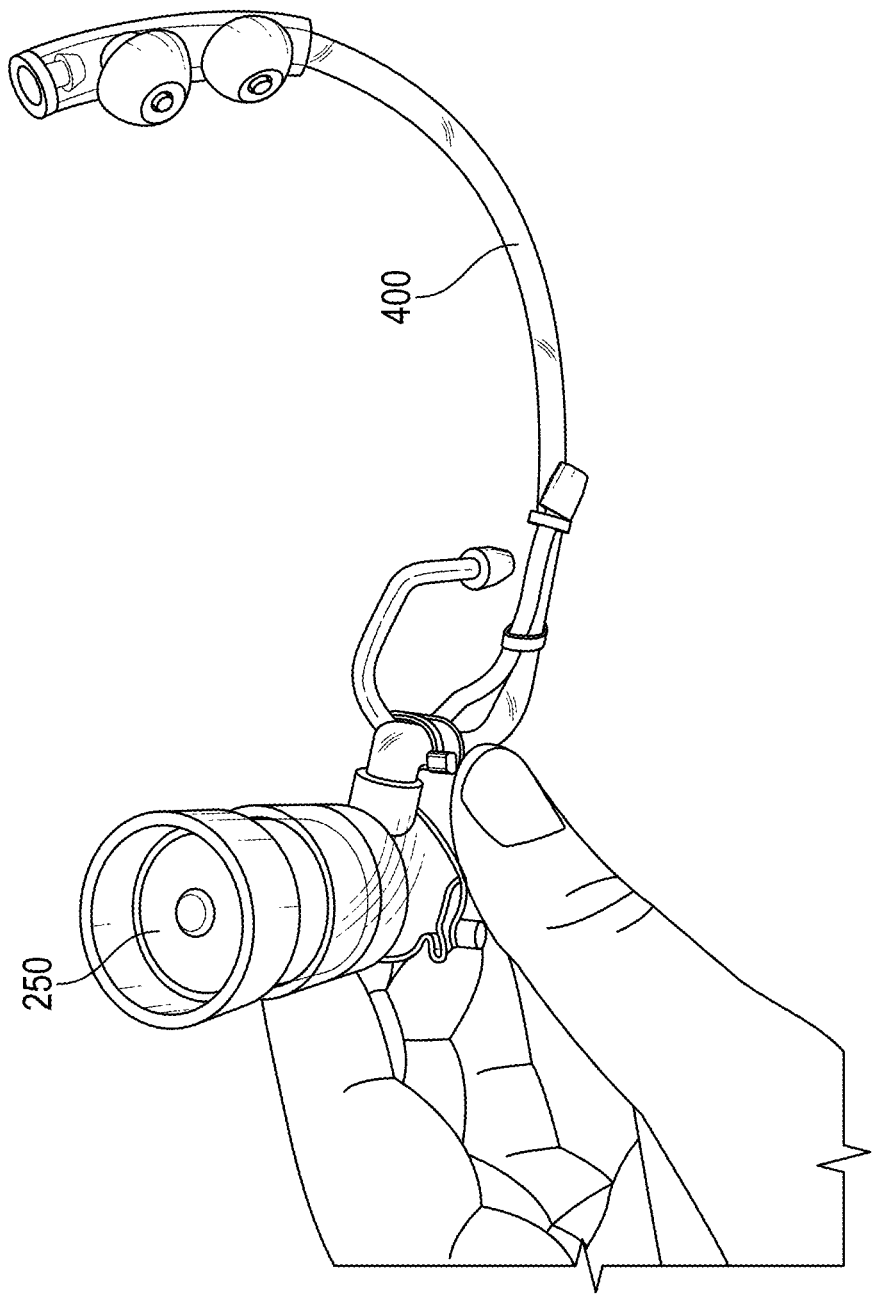
FIG. 12 depicts a perspective view of a disclosed embodiment

Referring to FIG. 12 a one-way valve 250 may be provided for effective air outflow on exhalation so the user doesn't have to strain to push air out through the filter upon exhaling. The valve can have a 'collar' around it to protect it from getting hair, etc. caught in the valve membrane, thereby preventing an airtight seal.

Figure 13:
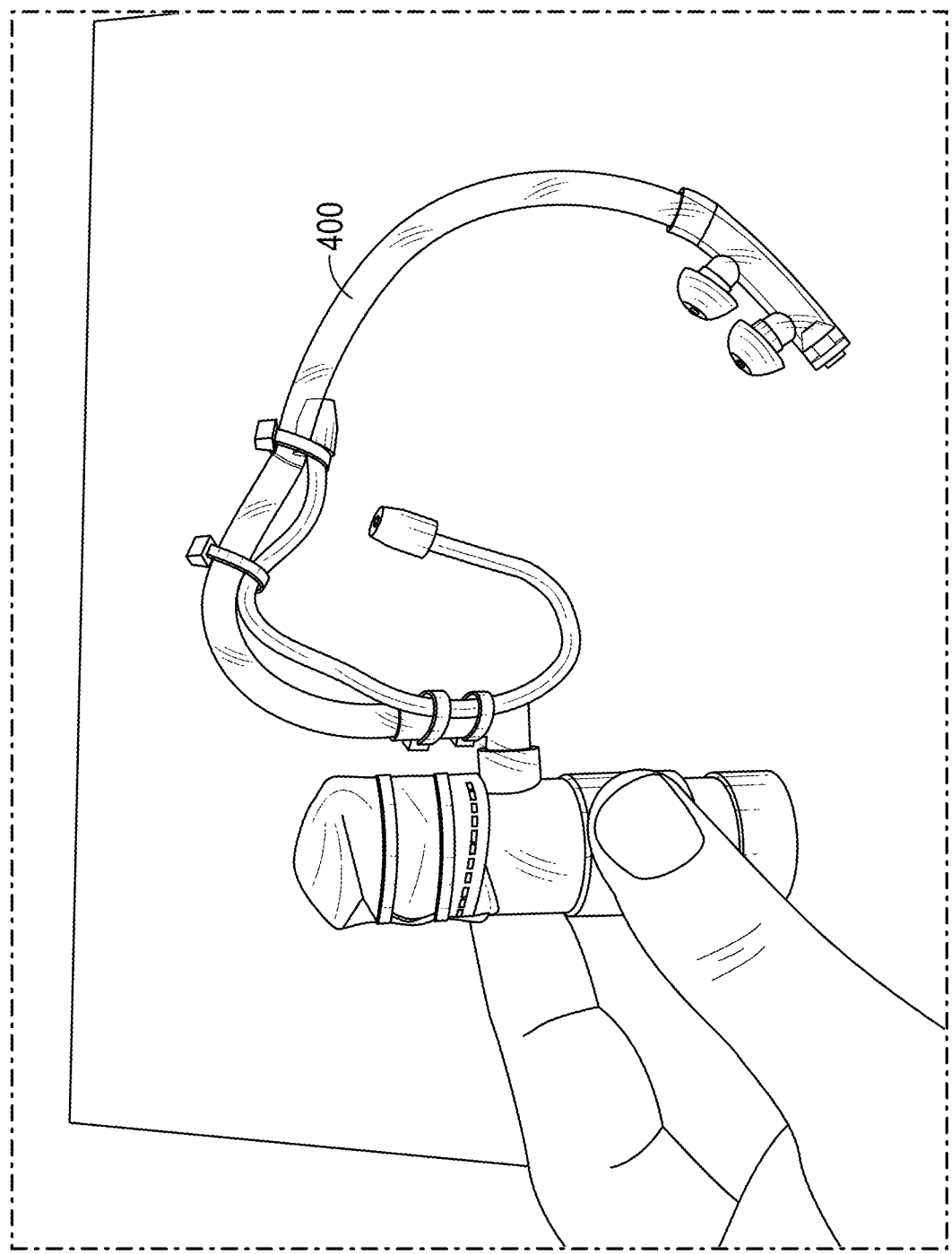
FIG. 13 depicts a perspective view of a disclosed embodiment

Referring to FIG. 13 a breathing tube 400 may connect to the air chamber and provides air flow to the cannular nasal insert, bridging across the cheek.

Figure 14:
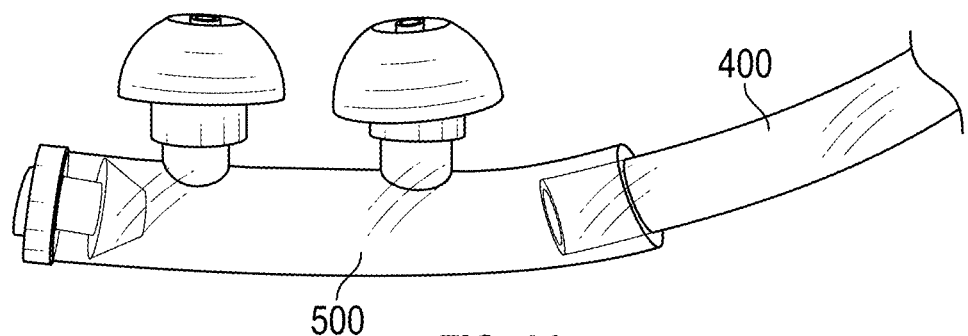
FIG. 14 depicts a nasal canula assembly
Figure 15:
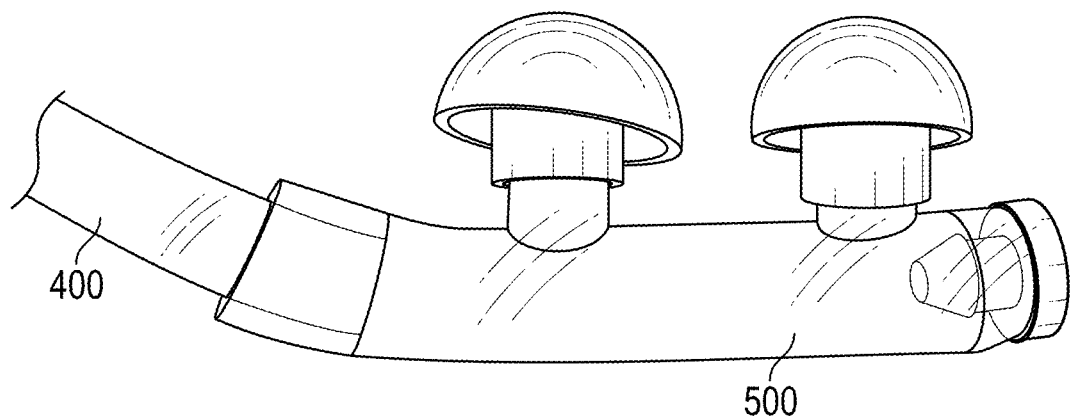
FIG. 15 depicts a nasal canula assembly
Figure 16:
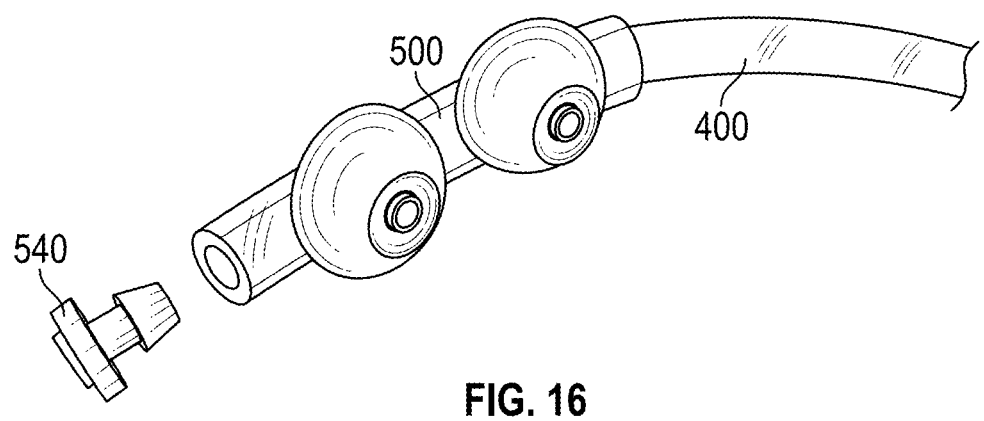
FIG. 16 depicts a nasal canula assembly
FIG. 17 disclosed embodiment in use
FIG. 18 disclosed embodiment in use
FIG. 19 disclosed embodiment in use
FIG. 20 disclosed embodiment in use
FIG. 21 a filter and air chamber assembly
FIG. 22 a filter and air chamber assembly
FIG. 23 air chamber assembly
Figure 17:
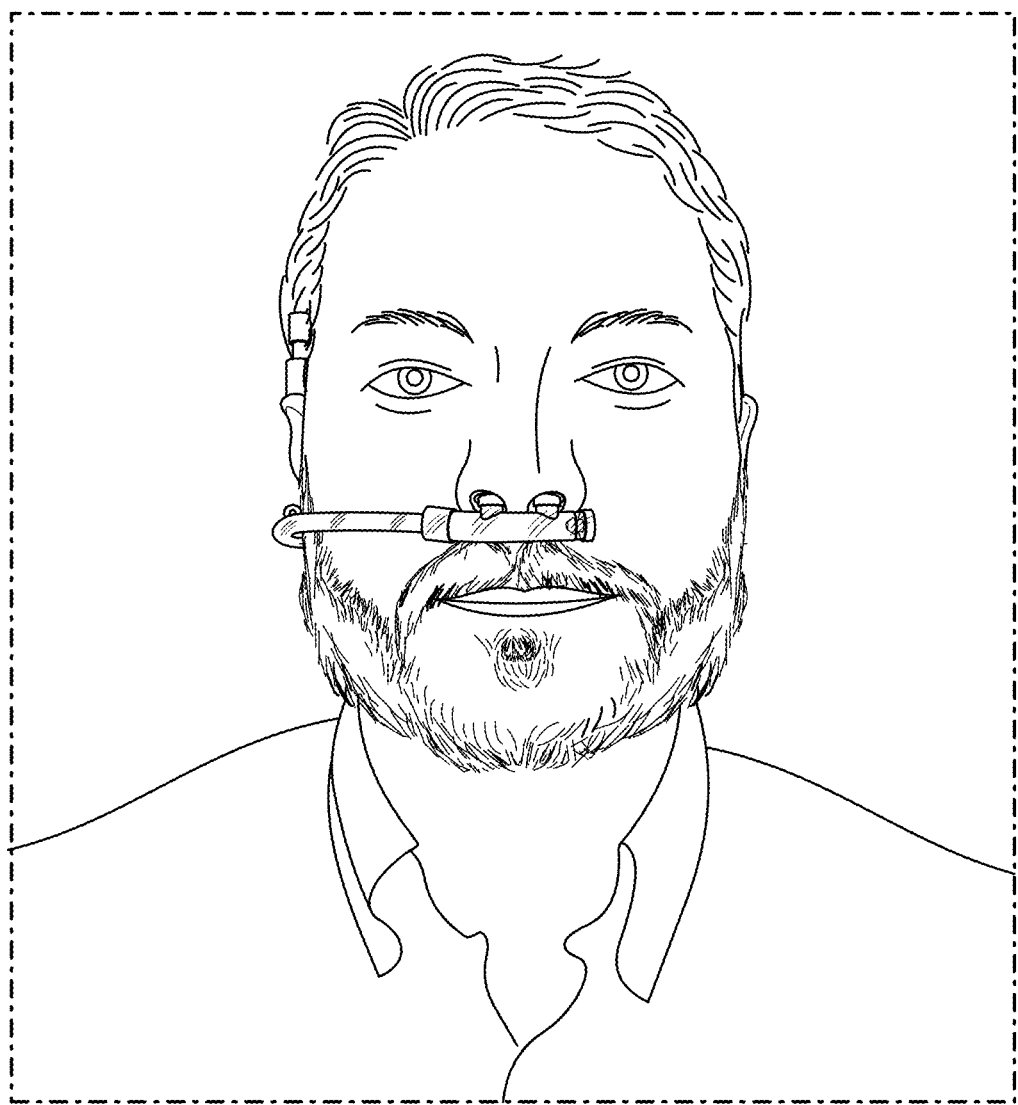
Figure 18:
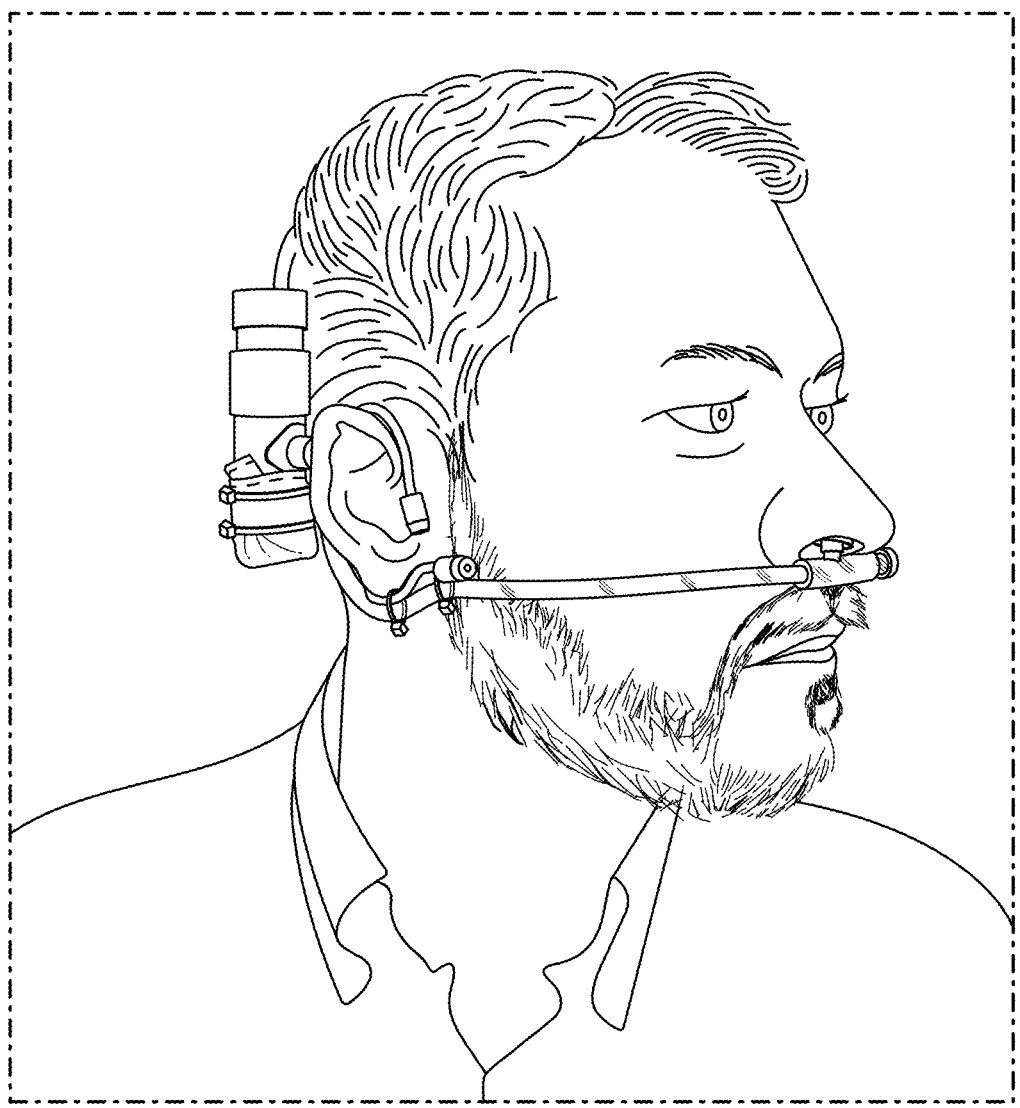
Figure 19:
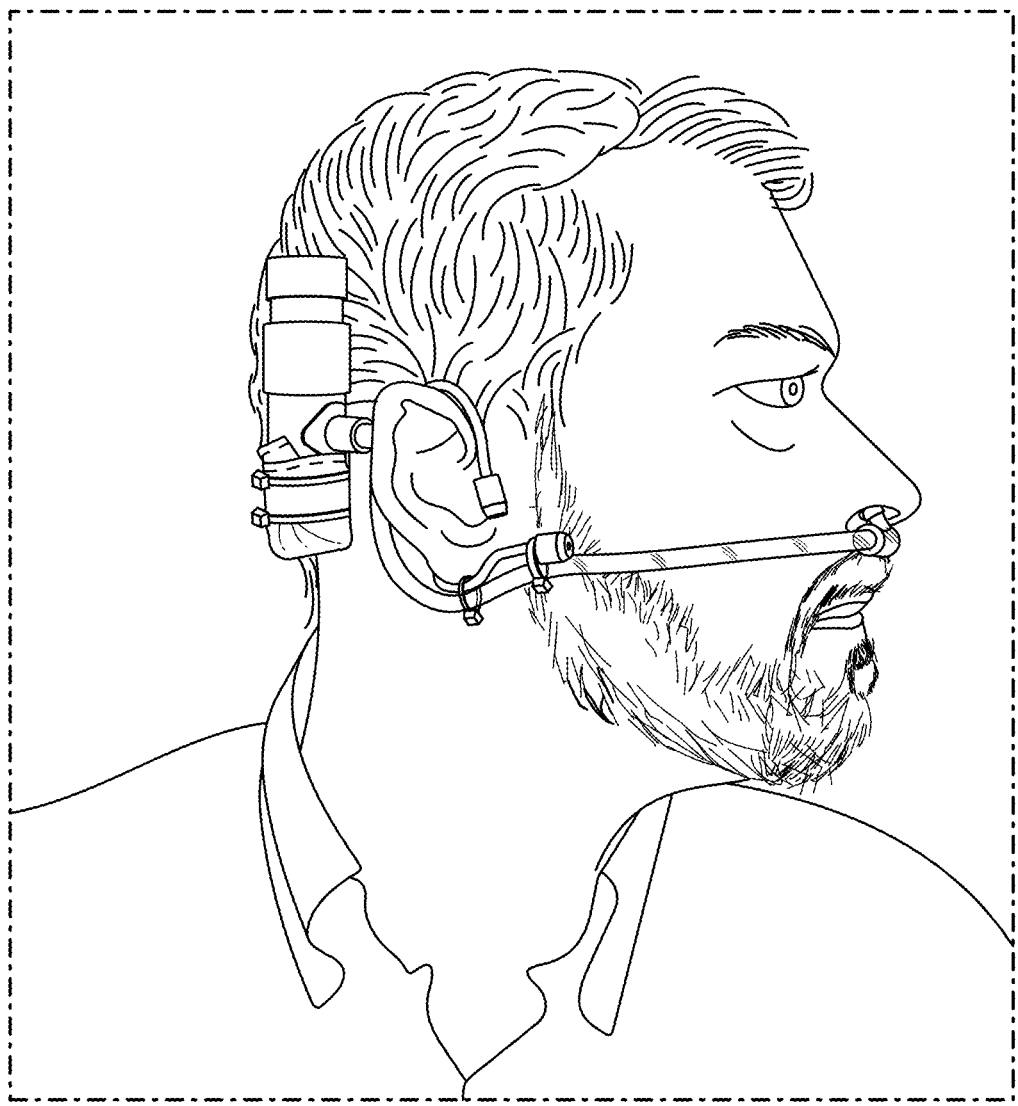
Figure 20:
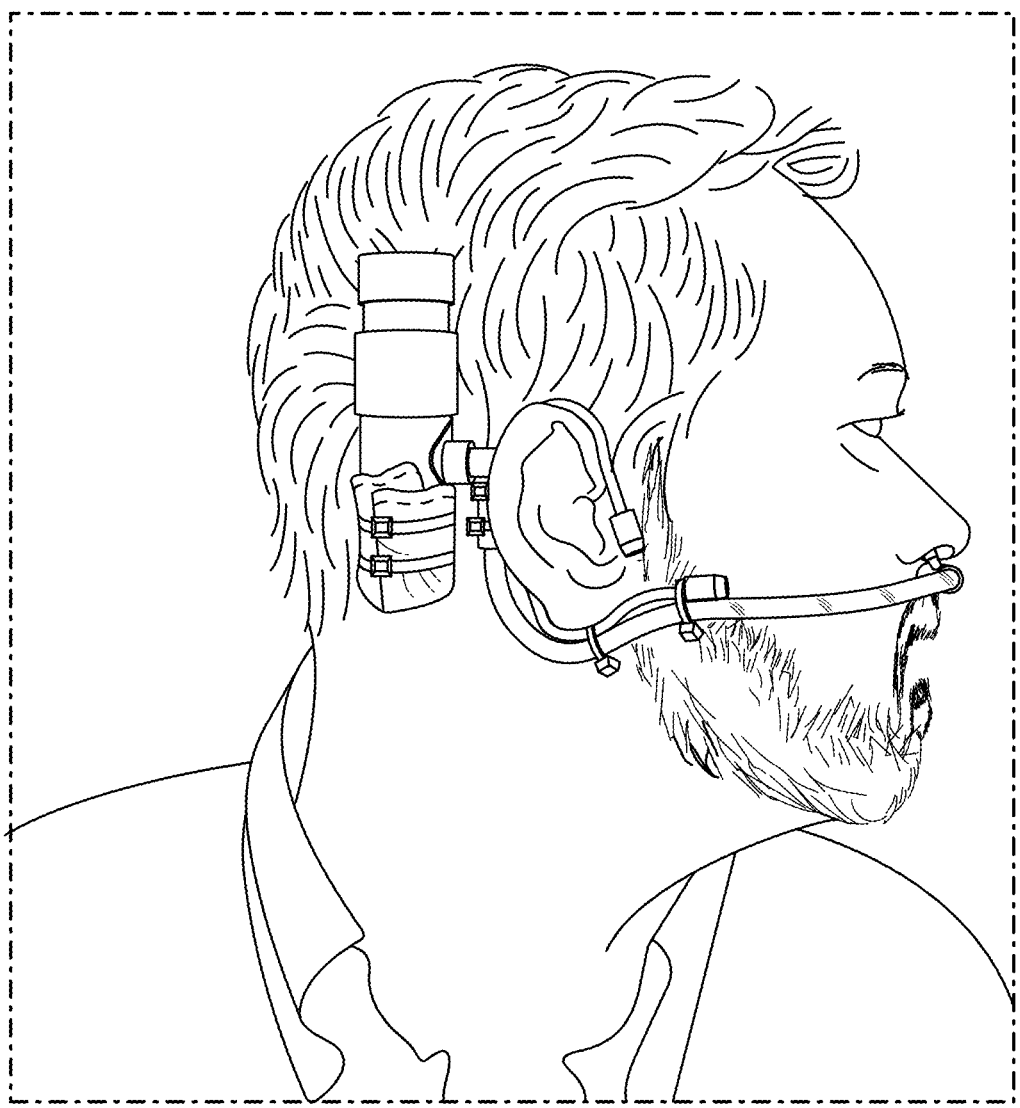

Referring to FIGS. 14, 15 and 16, a nasal cannula 500 may connect to the breathing tube and features an 'inverted cup' type flange on each of the nasal insert prongs, which provides for an intra-nasal airtight seal while also providing mounting support to keep the cannula secured in place below the nose. These flanges can come in multiple shapes (i.e. round, oval, etc.) to accommodate different shaped and sized nostrils.

A cannula plug 540 may comprise an airtight plug is featured on the cannula opposite to the breathing tube connection, which can be removed to allow for removal of moisture during prolonged use and allows the device to dehumidify and/or be cleaned when not in use.

Figure 21:
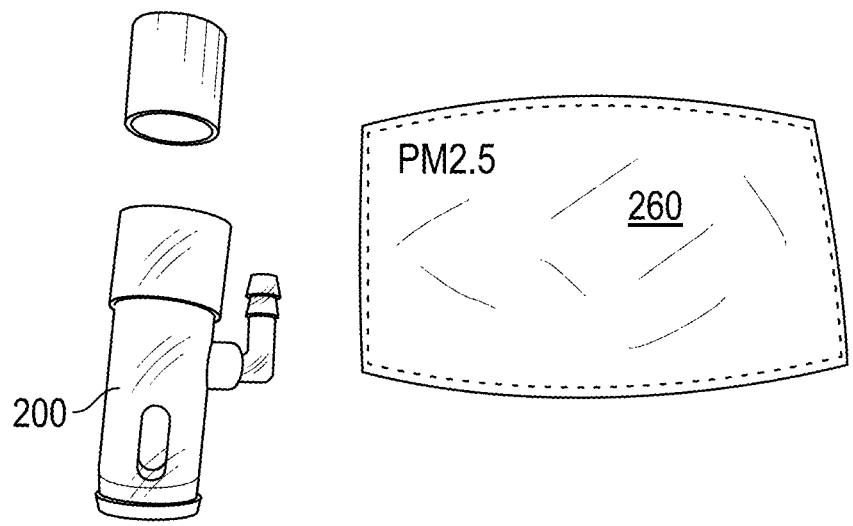
Figure 22:
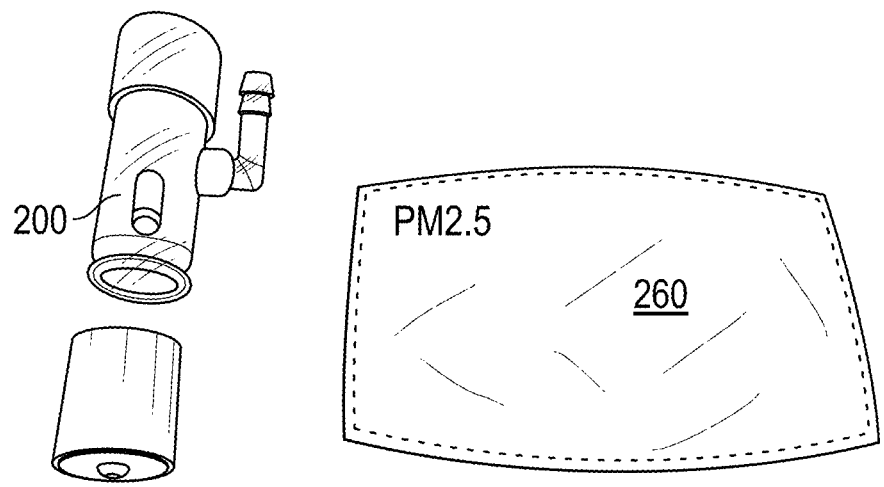

Referring to FIG. 21 and FIG. 22, a replaceable air filter 250 may comprise a 'bag' filter (single closed-end sleeve-type filter, or simple a circular shape filter) made from standard, rated filter materials (such as PM 2.5), that slips over the Filter Mount and is sealed at the bottom of the mount, providing an air-tight seal. This filter can be sealed by a number of means, such as a locking ring, restraint tie (i.e. zip tie), or a simple elastic band—all off of which provide for very easy replacement of the filter.

Figure 23:
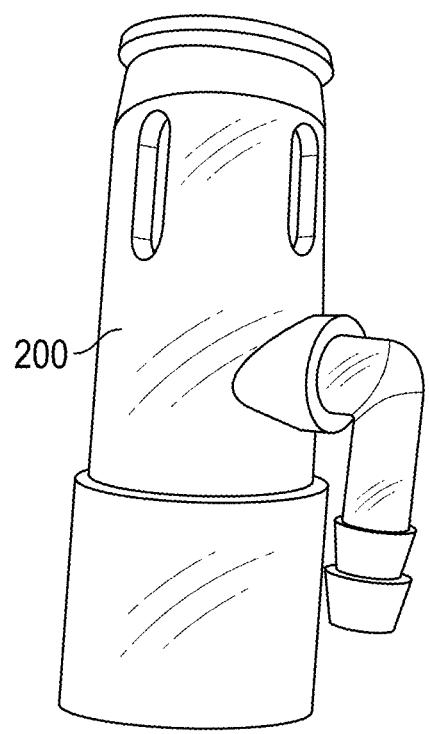

Referring to FIGS. 21 to 23, depictions of the air chamber disassembled are presented. You can see the ventilation slots cut out of the chamber housing in addition to the open top of the chamber. The one-way valve is a simple valve design in this prototype and can be seen removed from the air chamber (with the collar on top of the valve removed for clarity). A PM 2.5 filter was used in this prototype; cut to size and shaped around the air chamber in a bag configuration and secured by zip ties.

In addition to all the benefits described above, the Device requires, and thereby promotes, nasal breathing while in use. Nasal breathing has been shown by medical science, and has been known for hundreds of years, to promote a range of health benefits as opposed to mouth breathing.

The Device is very lightweight, comfortable, easy to use and maintain, cost effective, and can be used in a very wide range of environments and circumstances where one is concerned with filtering the ambient air for harmful particulate matter.

What is claimed is:

1. An ear mounted cannular nasal breathing filter system (100) comprising:
   a) an air chamber housing (200) comprising a cylindrical or other volumetric shape having an open top end with a top portion comprising a support structure (252) with the support structure attached to a one-way valve (250); the air chamber housing further comprising a lower portion defining a plurality of ventilation ports (220), with the ventilation ports covered by an air filter (262) the air filter made of cloth; an inside bottom surface of the one-way valve and an inside upper surface of a bottom portion of the air filter defining a mixing chamber (205); the mixing chamber in fluid connection with the one-way valve and the air filter; the mixing chamber configured to function as an air reservoir to recycle conditioned air of exhalation breaths;
   b) a horizontal air intake pipe (270) in fluid connection with the mixing chamber, a vertical air intake pipe (275) in fluid connection with the horizontal air intake pipe;
   c) a breathing tube (400) in fluid connection with the vertical air intake pipe;
   d) a nasal cannula assembly (500) in fluid connection with the breathing tube, the nasal cannula assembly comprising a main tube (505) in fluid connection with two prong posts (510) with each of the two prong posts in fluid connection with a prong flange (520)
   e) an ear mount attached to the vertical air intake pipe.

2. The system of claim 1 wherein the ear mount is a solid ear mount (310) comprising an upper arm (320) in slidable attachment to a lower arm (340) the upper arm and lower arm in further attachment by an elastic member (350).

3. The system of claim 1 wherein the ear mount is a flexible ear mount (300) attached to the vertical air intake pipe.

4. The system of claim 2 wherein the solid ear mount is further attached to the breathing tube.

5. The system of claim 2 wherein the solid ear mount is configured to rest upon a user's ear join.

6. The system of claim 2 wherein the elastic member of the solid ear mount is configured to compress the upper arm and lower arm into a user's ear join.

* * * * *